United States Patent
DeFelice et al.

(10) Patent No.: US 10,143,555 B2
(45) Date of Patent: Dec. 4, 2018

(54) CUSTOMIZED IMPLANTS FOR BONE REPLACEMENT

(71) Applicants: Scott DeFelice, Holyoke, MA (US); Anthony DeCarmine, Lebanon, CT (US)

(72) Inventors: Scott DeFelice, Holyoke, MA (US); Anthony DeCarmine, Lebanon, CT (US)

(73) Assignee: Oxford Performance Materials, LLC, South Windsor, CT (US)

( * ) Notice: Subject to any disclaimer, the term of this patent is extended or adjusted under 35 U.S.C. 154(b) by 209 days.

(21) Appl. No.: 14/815,348

(22) Filed: Jul. 31, 2015

(65) Prior Publication Data

US 2015/0351915 A1 Dec. 10, 2015

Related U.S. Application Data

(63) Continuation of application No. 13/058,905, filed as application No. PCT/US2009/053104 on Aug. 7, 2009, now abandoned.

(60) Provisional application No. 61/088,838, filed on Aug. 14, 2008.

(51) Int. Cl.
| | |
|---|---|
| *A61K 9/00* | (2006.01) |
| *A61F 2/30* | (2006.01) |
| *B33Y 80/00* | (2015.01) |
| *A61F 2/28* | (2006.01) |
| *A61L 27/16* | (2006.01) |
| *A61L 27/54* | (2006.01) |
| *A61L 27/56* | (2006.01) |
| *B29C 64/153* | (2017.01) |
| *B29K 71/00* | (2006.01) |
| *B29L 31/00* | (2006.01) |

(52) U.S. Cl.
CPC ............ *A61F 2/30771* (2013.01); *A61F 2/28* (2013.01); *A61F 2/30942* (2013.01); *A61L 27/165* (2013.01); *A61L 27/54* (2013.01); *A61L 27/56* (2013.01); *B29C 64/153* (2017.08); *B33Y 80/00* (2014.12); *A61F 2002/3092* (2013.01); *A61F 2002/3093* (2013.01); *A61F 2002/3097* (2013.01); *A61F 2002/30774* (2013.01); *A61F 2002/30784* (2013.01); *A61F 2002/30838* (2013.01); *A61F 2002/30948* (2013.01); *A61F 2002/30952* (2013.01); *A61F 2002/30962* (2013.01); *A61F 2002/30968* (2013.01); *A61F 2240/002* (2013.01); *A61L 2300/602* (2013.01); *A61L 2430/02* (2013.01); *B29K 2071/00* (2013.01); *B29L 2031/7532* (2013.01)

(58) Field of Classification Search
CPC .................................................. A61F 2/30771
See application file for complete search history.

(56) References Cited

U.S. PATENT DOCUMENTS

| | | | |
|---|---|---|---|
| 6,772,026 | B2 | 8/2004 | Bradbury et al. |
| 7,270,679 | B2 | 9/2007 | Istephanous et al. |
| 8,012,217 | B2 | 9/2011 | Strzepa et al. |
| 2001/0051833 | A1 | 12/2001 | Walter et al. |
| 2003/0006534 | A1 | 1/2003 | Taboas et al. |
| 2004/0236424 | A1 | 11/2004 | Berez et al. |
| 2006/0134419 | A1 | 6/2006 | Monsheimer et al. |
| 2007/0198022 | A1 | 8/2007 | Lang et al. |
| 2008/0206297 | A1 | 8/2008 | Roeder et al. |
| 2008/0221533 | A1 | 9/2008 | Matityahu |
| 2008/0258330 | A1 | 10/2008 | Muller et al. |

FOREIGN PATENT DOCUMENTS

WO     2010019463 A1    2/2010

OTHER PUBLICATIONS

Guaadaoui, What is a bioactive compound? A combined definition for a preliminary consensus, International Journal of Nutrition and Food Sciences, 2014, 3(3), 174-179.*
Dr. Stuart Green, Carbon Fibre Reinforced PEEK-OPTIMA Composite Materials for use in Surgical Implant Applications, Apr. 2006, Invibio PEEK Biomaterial Solutions.
European Search Report Application No. EP 09 08 7104 Completed: Sep. 5, 2013; dated Sep. 12, 2013 6 pages.
"Regenerex Porous Titanium Construct", 2008 Biomet Orthopedics, Warsaw, IN.

* cited by examiner

*Primary Examiner* — Paul W Dickinson
(74) *Attorney, Agent, or Firm* — Whitmyer IP Group LLC

(57) ABSTRACT

The present invention relates to customized implants for bone replacement that are prepared from poly(ether ketone ketone) or PEKK, and to a computer-based imaging and rapid prototyping (RP)-based manufacturing method for the design and manufacture of these customized implants. The PEKK customized implants made using rapid prototyping demonstrate biomechanical properties similar (if not identical) to that of natural bone even when prepared without the use of processing aids such as carbon black and aluminum powder.

25 Claims, No Drawings

CUSTOMIZED IMPLANTS FOR BONE REPLACEMENT

FIELD OF THE INVENTION

The present invention generally relates to customized implants for bone replacement that are prepared from poly (ether ketone ketone) or PEKK, and to a computer-based imaging and rapid prototyping (RP)-based manufacturing method for the design and manufacture of these customized implants.

BACKGROUND OF THE INVENTION AND SUMMARY OF THE INVENTION

Bone is composed of two kinds of tissue, exterior tissue which is dense in texture (compact tissue) and interior tissue that consists of slender fibers and lamellae that together form a lattice-type structure (cancellous tissue). Damage or loss of bone can result from trauma, congenital anomaly, pathologic conditions (e.g., rheumatoid arthritis, scleroderma, acromegaly and Gauchers disease), and surgical procedures.

In conventional treatment of bone defects, bone-derived or synthetic biomaterials are used to restore form and function. These biomaterials are preferably in the form of porous implant structures having interconnected porous spaces across the substratum of the implant. This allows bone growth into the porous spaces of the implant, securing its incorporation and osteointegration with the surrounding or adjacent viable bone at the margins of the bone defect.

Porous implant structures may be fabricated by a number of manufacturing routes. For implants made according to a standardized format (i.e., not customized for a particular individual) many conventional fabrication techniques can be used, including casting (e.g., ceramic-mold casting, centrifugal casting, die casting, investment casting, lost foam casting, permanent-mold casting, plaster-mold casting, pressure casting, sand casting, shell mold casting, slip casting, squeeze casting, slush casting, vacuum casting), extrusion, laser cutting, machining (e.g., electrochemical machining, water-jet machining), molding (e.g., blow molding, compression molding, injection molding, powder injection molding), thermoforming, and the like.

Implants may also be custom designed using computer-based imaging, processing and modeling techniques to convert common medical images into customized 3D renderings or Computer-Aided Design (CAD) models, which may then be used to fabricate the implant using any number of computer driven manufacturing techniques. The CAD models may be derived from any number of medical diagnostic imaging systems such as computed tomography (CT), magnetic resonance imaging (MRI), positron emission tomography (PET), and x-ray scans. Examples of computer driven manufacturing techniques include fused deposition modeling (FDM), selective laser sintering (SLS), and selective mask sintering (SMS).

Regardless of the manufacturing route, the resulting implant may then be subjected to one or more post-processing steps, which include modifying the implant to include pre-tab holes and other features that aid in rigid affixation.

Examples of synthetic biomaterials used in the fabrication of porous implant structures include ceramics and polymers such as polyethylene, polytetrafluoroethylene (PTFE) and poly(ether ether ketone) (PEEK).

By the late 1990s, PEEK emerged as the leading biomaterial for implants, first being offered commercially as a biomaterial for implants in April 1998. Bolstered by the existence of a stable supply of PEEK in the marketplace, research on PEEK biomaterials has and continues to flourish.

Customized PEEK scaffolds that are fabricated using CAD and rapid prototyping (RP) techniques are described in M. W. Naing et al., FABRICATION OF CUSTOMISED SCAFFOLDS USING COMPUTER-AIDED DESIGN AND RAPID PROTOTYPING TECHNIQUES, Rapid Prototyping Journal, vol. 11, pages 249-259 (2005). In this publication, PEEK-hydroxyapatite (HAP) biocomposite blends are sintered in SLS, with the advantages of HAP reinforced PEEK composites being identified as their strength and stiffness, which are reportedly compatible to that of the bone. PEEK™ 150XF finely ground PEEK powder is used to make these layered scaffolds.

Unfortunately, PEEK processing temperatures are quite high. In addition, less than favorable compressive residual stress profiles have been observed in these customized PEEK scaffolds, attributed to the relatively high solidification rates demonstrated by PEEK materials. Moreover, achieving and maintaining homogeneity in PEEK-HAP powder blends is difficult, with a lack of homogeneity causing the formation of HAP particle clusters in the powder blend. Localized heating of these HAP particle clusters have been found to result in the partial degradation of PEEK and/or the formation of microscale thermal stresses in the resulting scaffold.

By way of the present invention, it has been discovered that poly (ether ketone ketone) or PEKK may be used to make customized implants for bone replacement using rapid prototyping. PEKK offers the benefit of lower solidification rates, and in some embodiments, may also offer the added benefit of considerably lower processing temperatures.

It has also been discovered that customized implants for bone replacement that are prepared from PEKK using rapid prototyping demonstrate biomechanical properties similar (if not identical) to that of natural bone even when prepared without the use of processing aids such as carbon black and aluminum powder. In other words, these implants meet desired shape and strength requirements, which are typically expressed in terms of geometric size and shape, minimum wall thickness and minimum load bearing capacity.

The present invention specifically provides a laser-sinterable PEKK powder product. The laser-sinterable powder is comprised of a PEKK compound resin prepared from semi-crystalline and/or quasi-amorphous PEKK resin, and one or more fillers or additives selected from the group of glass, carbon and mineral fillers. By a "semi-crystalline" or "substantially crystalline" is meant a resin which has at least 10% crystallinity as measured by DSC, preferably from about 15%-90%, and most preferably from about 15-35% crystallinity. By "quasi-amorphous" is meant a resin which has at most 2% crystallinity as measured by DSC. The laser-sinterable powder has an average particle size ranging from about 10 to about 150 microns (preferably, from about 20 to about 100 microns, more preferably, from about 50 to about 70 microns).

The present invention also provides customized implants for bone replacement that are prepared from PEKK using rapid prototyping. The phrase "rapid prototyping", as used herein, means the automatic construction of physical objects such as implants using sold freeform fabrication.

In a first contemplated embodiment, the customized implant is a rigid implant having an inner core and an outer layer, the inner core having a relatively low porosity of less than about 10%, rendering the implant suitable for replacing bone in load bearing applications such as the spine, long bone and hip. The inventive rigid implant demonstrates a compressive strength (ASTM #D695) or load bearing capability ranging from about 100 to greater than about 200 megapascals (MPa).

Preferably, at least 95% of the pores have a diameter in the range of from about 1 to about 500 microns. Individual pores may or may not be connected to each other.

The implant's outer layer and its inner core preferably match the corresponding regions of the bone to be replaced if that bone were healthy. In other words, the outer layer would approximate the morphologic traits of the compact tissue in the cortical layer of a similar healthy bone, while the inner core would approximate the morphologic traits of the cancellous tissue in the trabecular core of a similar healthy bone.

In a second contemplated embodiment, the customized implant is a less rigid implant with a substantially uniform cross-sectional morphology, which has a higher porosity of greater than about 35%. Such implants are suitable for replacing bone in partially load bearing applications such as scaffolding for ongrowth/ingrowth of tissues, support for stem cell media and the like.

Preferably, individual pores in this less rigid implant are connected to each other, the pores having a diameter in the range of from about 50 to about 250 microns.

The present invention also provides a CAD-based RP process for the design and manufacture of these customized implants, the process comprising:

(a) scanning a patient in an area requiring bone repair or replacement to obtain tomographic information;
(b) designing a bone implant model at a CAD terminal using the tomographic information obtained from the patient;
(c) optionally, modifying the bone implant model by, for example, adding suture anchors, threaded holes, mating surfaces and textures, open cell regions for scaffolding, surface pores to carry antibiotics, and/or varying density or porosity levels so as to vary stiffness or rigidity; and
(d) using a solid free-form fabrication method such as SLS to form a bone implant from the bone implant model, the bone implant comprising sequential layers of biocompatible PEKK.

In a preferred embodiment, a PEKK compound resin powder is used to form the bone implant, the PEKK powder having a preferred average particle size ranging from about 20 to about 100 microns (more preferably, from about 50 to about 70 microns).

In a more preferred embodiment, a SLS fabrication method is used to form the bone implant, the SLS fabrication method comprising heating a part bed to a temperature ranging from about 280° C. to about 350° C. and scanning a 0.015 to 1.5 Wattsec/millmeter (mm)$^2$ laser spot at selected locations of a layer of PEKK powder contained in the part bed.

Other features and advantages of the invention will be apparent to one of ordinary skill from the following detailed description. Unless otherwise defined, all technical and scientific terms used herein have the same meaning as commonly understood by one of ordinary skill in the art to which this invention belongs. All publications, patent applications, patents and other references mentioned herein are incorporated by reference in their entirety. In case of conflict, the present specification, including definitions, will control. In addition, the materials, methods, and examples are illustrative only and not intended to be limiting.

DETAILED DESCRIPTION OF THE INVENTION

Image based modeling involves three basic steps, namely, mage acquisition, image processing, and three dimensional reconstruction (3DR) to form voxels (basic unit of computed tomography reconstruction) that describe the 3D shape of the model for use in further and more advanced modeling, and subsequent manufacture.

As noted above, raw patient data in the form of noninvasive images of the area encompassing the diseased or damaged bone(s) may be acquired from any number of medical diagnostic imaging systems such as CT, MRI, PET, and x-ray scans.

Image processing and 3DR may be achieved using any suitable medical reconstructive and reverse engineering software such as MIMICS® software programs for processing and editing images for medical and surgical applications, which are available from Materialise N.V. Technologielaan 15, B-3001, Leuven, Belgium, and GEOMAGIC STUDIO® computer software for creating digitized models, which is available from Geomagic U.S., 3200 East Hwy 54, Cape Fear Building, Suite 300, Research Triangle Park, N.C., 27709.

Once loaded into the software, the raw patient data in the form of noninvasive images (which are typically in the form of slice images) are properly registered and aligned. Next, the region of interest (i.e., the diseased or damaged bone(s)) is identified and a 3D rendering or model is made. In a first contemplated embodiment, the 3D model, which is in the form of segmented information, is further customized and then exported to an RP machine using, for example, an RP Slice Module, which interfaces with MIMICS® software programs or GEOMAGIC STUDIO computer software and reportedly any kind of RP system. The RP Slice Module is available from Materialise N.V. In a second contemplated embodiment, the segmentation is transferred directly to an RP machine.

The 3D rendering or model may be enhanced and further customized by, for example, converting the 3D voxel dataset that describes the 3D shape of the model to point data form, cleaning the points (i.e., eliminating noise points), triangulating the points to form a faceted model, varying density or porosity levels, adding open cell regions for scaffolding, modeling the bone surface using freeform surfaces or NURBS patches, further refining and enhancing the surface (e.g., adding surface pores to carry antibiotics, adding suture anchors and/or threaded holes, mating surfaces and textures), etc. Design software suitable for enhancing and further customizing the 3D rendering or model includes software available from SolidWorks Corporation, 300 Baker Avenue, Concord, Mass. 01742, under the trade designation SOLIDWORKS® computer software.

The thus generated CAD models are saved in an IGES or STEP/STL format, which are neutral data formats that allow for transfer of the 3D rendering or CAD model between dissimilar systems, and then exported to an RP machine.

In a preferred embodiment, the RP machine is a powder-based SLS system. The system, which typically comprises two side powder cartridges, a platform with variable height, heaters and a laser source, produces 3D objects from sliced 3D CAD models using powdered materials with heat generated by the laser.

Although the CAD-based RP process for the design and manufacture of these customized implants will be described herein mainly in connection with SLS, the invention is not so limited. Other RP-based manufacturing methods such as fused deposition modeling (FDM) and Selective Mask Sintering (SMS) may be used to manufacture the inventive implant.

An SLS system suitable for use in the present invention comprises:
(a) a powder delivery system, for applying successive layers of PEKK power onto a target surface on a variable height part bed or platform;
(b) a laser for generating a laser beam;
(c) a scanning system for controllably directing the laser beam to a target plane at an uppermost surface of the powder layer; and
(d) a computer, coupled to the powder delivery system and scanning system, and programmed to perform a plurality of operations comprising: reading data from a CAD model, directing the powder delivery system to lay down successive layers of PEKK powder, and directing the scanning system to laser scan each such successive PEKK layer.

Preferably, the laser for generating a laser beam in the SLS system is a carbon dioxide ($CO_2$) laser source. Such SLS systems are available from EOS of North America Inc., 28970 Cabot Drive, Novi, Mich., 48377-2978, and from 3D Systems, 333 Three D Systems Circle, Rock Hill, S.C. 29730.

PEKK is used in either its pure form or with fillers or additives selected from the group including, but not limited to, surface-bioactive ceramics (e.g., hydroxyapatite (HAp), BIOGLASS® biologically active glass), resorbable bioactive ceramics (e.g., α-tricalcium phosphate (α-TCP), β-TCP), and solids that will render the implant or scaffold radioopaque (e.g., barium sulfate ($BaSO_4$)). Processing aids such as carbon black and aluminum powder are not employed in the subject invention.

In a first preferred embodiment, PEKK powder with an average particle size ranging from about 10 to about 150 microns is used in its pure form. Such powders are available from Oxford Performance Materials, Inc., 120 Post Rd., Enfield, Conn. 06082 ("Oxford Performance Materials"), under the product designation OXPEKK-IG PEKK powder.

In a second preferred embodiment, PEKK powder in the form of a compound resin powder with an average particle size ranging from about 10 to about 150 microns is used, the compound resin powder being prepared by melt blending a mixture of PEKK resin with from about 10 to about 40% by wt. of one or more fillers or additives (e.g., HAp, BIOGLASS® biologically active glass, α-TCP, β-TCP, $BaSO_4$) using conventional melt-blending techniques and then grinding the blended product to form a powder.

In operation, the platform used in the SLS system is heated to a temperature ranging from about 280° C. to about 350° C. (preferably, from about 280° C. to about 295° C. (for quasi-amorphous PEKK) or from about 335° C. to about 350° C. (for semi-crystalline PEKK)), and a thin layer of PEKK powder having an average particle size ranging from about 10 to about 150 microns (preferably, from about 20 to about 100 microns) is spread evenly onto the heated platform with a roller mechanism. Then, the powder is raster-scanned with the $CO_2$ laser beam (power density (energy per unit area and time)) ranging from about 0.015 to about 1.5 Wattsec/$mm^2$ (preferably, from about 0.1 to about 0.25 Wattsec/$mm^2$), with only the powder that is struck becoming fused. Successive layers of PEKK powder are then deposited and raster-scanned one on top of another until the implant or scaffold is complete. Each layer is sintered deeply enough to bond it to the underlying or preceding layer.

The customized implants of the present invention demonstrate biomechanical properties similar (if not identical) to that of natural bone. More specifically, the inventive implants have a compressive strength (ASTM #D695) or load bearing capability ranging from about 10 to greater than about 200 megapascals (MPa). This compressive strength provides load-bearing capability greater than typical cancellous bone and up to that of typical cortical bone. The inventive implants also have a flexural modulus (ASTM #D570) ranging from about 0.5 to greater than about 4.5 gigapascals (GPa).

For implants used to replace bone in load bearing applications such as the spine, long bone and hip, low porosity (i.e., less than about 10%) implants would be formed. These implants demonstrate compressive strength (ASTM #D695) or load bearing capability ranging from about 100 to greater than about 200 MPa and flexural modulus (ASTM #D570) ranging from about 3.5 to greater than about 4.5 GPa.

In one contemplated embodiment, the surface topography of the low porosity implant is altered and/or one or more through openings are added to encourage bone, vascular and nerve in-growth. As will be readily appreciated by one skilled in the art, such alterations or additions may be designed into the CAD model, or formed post-manufacture by drilling, cutting, punching, or other suitable means.

For implants used to replace bone in partially load bearing applications such as scaffolding for ongrowth/ingrowth of tissues, support for stem cell media and the like, a higher porosity implant (i.e., open cell-3D interconnected pores) would be formed. These implants demonstrate compressive strength (ASTM #D695) or load bearing capability ranging from about 10 to about 200 MPa and a flexural modulus (ASTM #D570) ranging from about 0.5 to about 4.5 GPa.

In one contemplated embodiment, the higher porosity implant is in the form of a three-dimensional lattice structure. The lattice structure, which is optimized for bone, vascular and nerve in-growth, has a plurality of bars crossing each other in a plurality of zones, the bars being fused in each of these zones. Interstitial spaces provided between adjacent bars define a plurality of interconnected pores or channels in the lattice structure.

The implant of the present invention may contain one or more porous reservoirs, which hold one or more therapeutic agents including, but not limited to, antibiotics, anti-coagulants, anti-inflammatory, anti-metabolites, antivirals, bone morphogenic proteins, cell adhesion molecules, growth factors, healing promotors, immunosuppressants, vascularizing agents, topical anesthetics/analgesics, and the like. These therapeutic agents may be prepared with carriers that will protect against rapid release (e.g., a controlled release vehicle such as a polymer, microencapsulated delivery system or bioadhesive gel). In one contemplated embodiment, the therapeutic agent is encapsulated by biocompatible, degradable polymers including, but not limited to, polyhydroxy adds such as polylactic add (PLA), polyglycolic add (PGA), and their copolymers (ALGA). These polymers are degraded by hydrolysis to products that can be metabolized and excreted.

The inventive implant may also be modified to include means for securing the implant to adjacent bony structures. For example, interfacial fastening mechanisms such as custom mating screws and fasteners may be designed into the CAD model, or formed/affixed post-manufacture.

While various embodiments of the present invention have been described above, it should be understood that they have been presented by way of example only, and not limitation. Thus, the breadth and scope of the present invention should not be limited by any of the exemplary embodiments.

What is claimed is:

1. An implant or scaffold for bone replacement composed exclusively of pure selectively laser sintered poly(ether ketone ketone) (PEKK), the implant or scaffold being capable of ongrowth/ingrowth of tissues, the implant or scaffold not comprising calcium phosphate.

2. An implant or scaffold for bone replacement, comprising laser sintered poly(ether ketone ketone) (PEKK), the implant or scaffold being capable of ongrowth/ingrowth of tissues, the implant or scaffold not comprising calcium phosphate.

3. The implant or scaffold of claim 2, further at least one feature selected from the group consisting of a) openings configured to encourage bone, vascular and nerve in-growth, b) surface pores configured to hold therapeutic agents, and c) surface anchors and/or threaded holes.

4. The implant or scaffold of claim 3, wherein said surface pores hold one or more therapeutic agents selected from the group consisting of antibiotics, anti-coagulants, anti-inflammatory, anti-metabolites, antivirals, bone morphogenic proteins, cell adhesion molecules, growth factors, healing promoters, immunosuppressants, vascularizing agents, and topical anesthetics/analgesics; said therapeutic agents optionally being present in or on a carrier for controlled release.

5. The implant or scaffold of claim 4, wherein said carrier is encapsulated in a biocompatible or biodegradable polymer, or in a bioadhesive gel.

6. The implant or scaffold of claim 1, comprising a rigid implant having an inner core with a low porosity of 10 percent or less pores and an outer layer, said implant having a compressive strength ASTM #D695 of from 100 to 200 megapascals (Mpa) and a flexural modulus ASTM #D570 of greater than 3.5 gigapascals (GPa).

7. The implant or scaffold of claim 6, wherein said implant replaces a load-bearing bone.

8. The implant or scaffold of claim 7, wherein said load-bearing bone is selected from a spine, a long bone of an arm or a leg, and a hip bone.

9. The implant or scaffold of claim 8, wherein at least 95 percent of pores have a diameter of 1-500 microns.

10. The implant or scaffold of claim 1, comprising a substantially uniform cross-sectional morphology having a porosity of greater than about 35 percent, wherein the pores are interconnected and have an average diameter of 50-250 microns, and wherein said implant or scaffold has a compressive strength ASTM #D695 of from 10 to 200 megapascals (Mpa) and a flexural modulus ASTM #D570 of from 0.5 to 4.5 gigapascals (GPa).

11. The implant or scaffold of claim 10, comprising a bone replacement scaffolding for ongrowth/ingrowth of tissues, or as a support for stem cells.

12. An implant or scaffold comprising a laser sintered composition comprising pure poly(ether ketone ketone) (PEKK) the implant or scaffold not comprising calcium phosphate, wherein said powder has an average particle size of from 10-150 microns, and is either a) semi-crystalline, having at least 10% crystallinity by weight as measured by DSC, or said powder is b) quasi-amorphous, at most 2% crystallinity as measured by DSC.

13. The implant or scaffold of claim 10, comprising a three-dimensional lattice structure having a plurality of bars crossing each other in a plurality of zones, the bars being fused in each of the zones, wherein the interstitial spaces between adjacent bars define a plurality of interconnected pores or channels in the lattice structure.

14. An implant or scaffold comprising a laser sintered composition composed exclusively of pure poly(ether ketone ketone) (PEKK) powder, the implant or scaffold not comprising calcium phosphate, wherein said powder has an average particle size of from 10-150 microns, and is either a) semi-crystalline, having at least 10% crystallinity by weight as measured by DSC, or said powder is b) quasi-amorphous, at most 2% crystallinity as measured by DSC.

15. The laser sinterable composition of claim 12, wherein said composition further comprises one or more fillers selected from the group consisting of glass, carbon, mineral fillers, surface-bioactive ceramics, solids that will render the implant or scaffold radioopaque, and barium sulfate ($BaSO_4$).

16. The laser sinterable composition of claim 14, wherein said powder has an average particle size of from 20-100 microns.

17. The laser sinterable composition of claim 14 wherein said semi-crystalline powder has 15-90% crystallinity as measured by DSC.

18. The laser sinterable composition of claim 14, wherein said powder has an average particle size of from 50-70 microns.

19. The laser sinterable composition of claim 14 wherein said semi-crystalline powder has 15-35% crystallinity as measured by DSC.

20. A process for producing a customized implant or scaffold for bone replacement comprising the steps of:
 (a) scanning a patient in an area requiring bone repair or replacement to obtain tomographic information;
 (b) designing a bone implant model using computer aided design from the tomographic information obtained from the patient;
 (c) optionally, modifying the bone implant model by one or more of the following steps: adding suture anchors, threaded holes, mating surfaces and textures, open cell regions for scaffolding, surface pores to carry antibiotics, and/or varying density or porosity levels so as to vary stiffness or rigidity; and
 (d) forming a bone implant or scaffold using a solid free-form fabrication method from the bone implant model, the bone implant being composed of sequential layers of biocompatible pure laser sintered poly(ether ketone ketone) (PEKK) powder, said implant or scaffold being capable of ongrowth/ingrowth of tissues said implant or scaffold not comprising calcium phosphate.

21. The process of claim 20, wherein said fabrication method in step (d) is by selective laser sintering (SLS).

22. The process of claim 20, wherein the PEKK powder has an average particle size of from 10 to 150 microns.

23. The process of claim 20, wherein said PEKK powder further comprises from 5 to 40 weight percent of additives, based on the weight of PEKK.

24. The process of claim 23, wherein said additives are selected from the group consisting of solids to render the implant or scaffold radioopaque.

25. The implant or scaffold of claim 1, wherein the implant or scaffold has openings to encourage bone, vascular, and nerve growth.

* * * * *